(12) United States Patent
Yoder

(10) Patent No.: US 7,332,151 B2
(45) Date of Patent: Feb. 19, 2008

(54) LIQUID ANIMAL HOOF CONDITIONER

(76) Inventor: Ben Ray Yoder, N. 4825 Highway 104, Brodhead, WI (US) 53520

( * ) Notice: Subject to any disclaimer, the term of this patent is extended or adjusted under 35 U.S.C. 154(b) by 201 days.

(21) Appl. No.: 10/856,523

(22) Filed: Jun. 1, 2004

(65) Prior Publication Data

US 2005/0266103 A1 Dec. 1, 2005

(51) Int. Cl.
*A61K 36/55* (2006.01)
*A61K 36/886* (2006.01)
*A61K 36/00* (2006.01)

(52) U.S. Cl. .................. 424/61; 424/725; 424/744; 252/519.32

(58) Field of Classification Search .................. None
See application file for complete search history.

(56) References Cited

U.S. PATENT DOCUMENTS

| 4,182,340 A | 1/1980 | Spencer |
| 4,765,411 A | 8/1988 | Tennant |
| 4,822,595 A * | 4/1989 | Corliss et al. ................ 424/61 |
| 4,896,727 A | 1/1990 | Busser |
| 5,069,289 A | 12/1991 | Schaffer |
| 6,364,025 B1 | 4/2002 | Jacobs |
| 6,412,566 B1 | 7/2002 | Rovelli et al. |

\* cited by examiner

*Primary Examiner*—Patricia Leith
(74) *Attorney, Agent, or Firm*—Theresa M. Seal

(57) ABSTRACT

A liquid animal hoof conditioner for moisturizing, protecting and preventing animal hoofs, especially those of horses, from developing painful and debilitating cracks, such as quarter cracks and sand cracks, and for healing such cracks after they occur, includes whole leaf aloe vera, flax seed oil, turpentine, pine tar, and an emulsifier in a composition that can be easily brushed onto the horse's hoof without any inconvenience or discomfort to the horse so that the hoof can naturally heal over a period of time. The animal hoof conditioner can also be applied to the hoofs on a regular basis for hoof maintenance during the dry summer months.

2 Claims, 2 Drawing Sheets

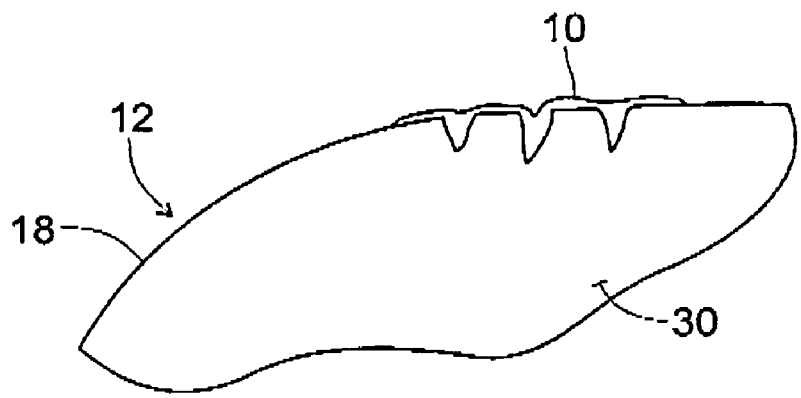
Fig. 3
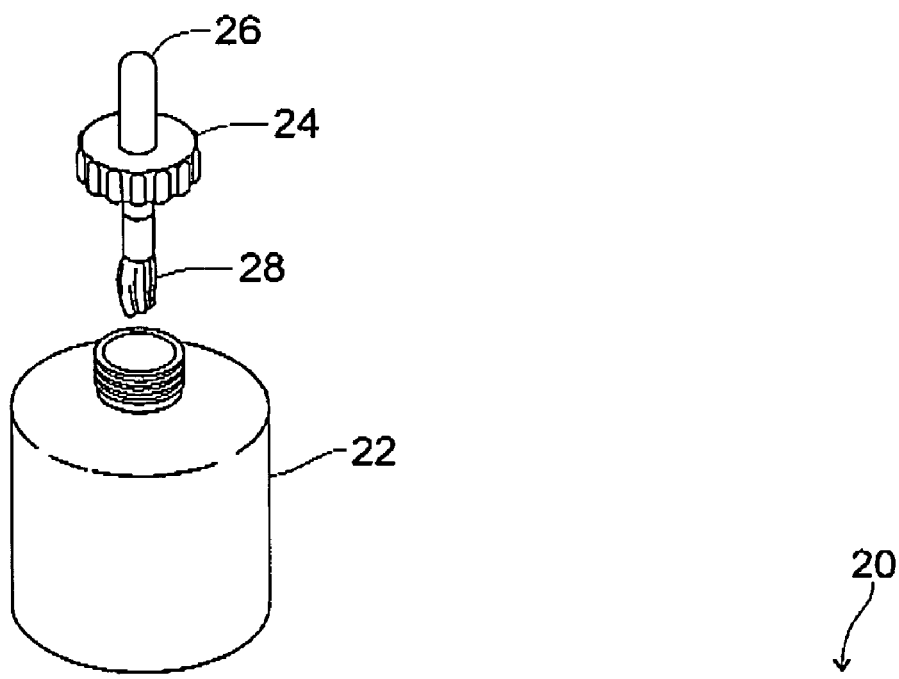
Fig. 4
INGREDIENTS
39.75% Aloe Vera
19.75% Flax Seed Oil
19.75% Turpentine
19.75% Pinetar
1.00% Emulsifier
Fig. 5

LIQUID ANIMAL HOOF CONDITIONER

FIELD OF THE INVENTION

The present invention pertains to animal hoof protection and repair methods and compositions, and more particularly pertains to a liquid conditioner for protecting, repairing and healing animal, and especially horse, hooves.

BACKGROUND OF THE INVENTION

Various types of animals, such as equines and ungulates, have hooves that grow much like human nails and thus require regular care and maintenance. This is especially the case with horses that are regularly fitted with shoes, such as riding horses and show horses. The shoes are secured to the hoofs by nails that are driven upwardly into the hoofs. Like all appendages, nerves and blood vessels circulate through the hoofs for carrying nutrients, oxygen and for the transmission of sensory stimulation.

The hoofs require continual care so as to avoid and prevent foot injuries; and thus a common activity for all horse owners and farriers is trimming the hoofs in the same manner that the nails of a human being are trimmed. In addition, the hoofs must be continuously checked and cleaned of grit, sand, gravel, stones, pebbles and other debris that has accumulated in the frog area or into any gaps or cracks on the hoof surface or between the shoe and the underside of the hoof. Among the most painful and potentially debilitating types of cracks that occur are cracks called quarter cracks that run vertically along the hoof. Because the hoof is a continually growing appendage, there is no way to actually close the crack; generally the only course of action is to prevent the further extension of the crack keeping the hoof properly trimmed as the continuous growth of the hoof eventually causes the crack to grow out.

Due to the great time and expense that horse owners and breeders invest in their animals, the prior art reveals a range of devices and methods for both shoeing hoofed animals, and for maintaining the condition and health of the animals' hooves.

For example, the Spencer patent (U.S. Pat. No. 4,182,340) discloses a horse hoof repair kit that includes extending a suture through opposite side of a crack in the horse's hoof, filling the crack with an adhesive material and then placing the hoof in a bag that applies pressure to the adhesive to facilitate the curing of the adhesive.

The Tennant patent (U.S. Pat. No. 4,765,411) discloses a method of making a horseshoe that includes placing the hoof in a mold, filling the mold with a plastic acrylic material, and then curing the material by exposure to UV light so that the material integrally bonds to the hoof.

The Busser patent (U.S. Pat. No. 4,896,727) discloses a method of repairing the horse's hoof that includes the use of a synthetic resin and filler particles that are cured by addition of a hardening catalyst and an accelerator The Schaffer patent (U.S. Pat. No. 5,069,289) discloses a process for repairing a crack in a horse's hoof or attaching a shoe to the hoof that includes heating a urethane liquid so that a phase change occurs increasing the bonding action for attaching a shoe to the hoof or for repairing a crack in the hoof.

The Rovelli et al. patent (U.S. Pat. No. 6,412,566 B1) discloses a horse hoof protection method that includes injecting a rapidly curing synthetic organic resin adherent into the open volume at the hoof bottom wall so that the resin adherent can cure and fill the open volume thereby protecting the sensitive area of the hoof bottom wall.

The Jacobs patent (U.S. Pat. No. 6,364,025 B1) discloses a method of protecting a horse's hoof that includes compositions that are combined from separate cartridges for injection into the open volume of the hoof bottom wall thereupon forming a rapidly curing organic resin that hydraulically fills the open volume.

Nonetheless, despite the ingenuity of the above methods and compositions, there remains a need for a method and composition for repairing and protecting animal hooves that is easy to apply and is not uncomfortable to the animal during application.

SUMMARY OF THE INVENTION

The present invention comprehends a liquid hoof conditioner for animals, with an emphasis for application on equine hoofs, to moisturize and condition hoofs in order to prevent cracks, such as sand cracks and quarter cracks, from occurring, and to heal existing cracks and to prevent the further cracking of the hoofs.

The ingredients of the liquid animal hoof conditioner include whole leaf aloe vera, linseed oil, turpentine, pine tar, and an emulsifier. The animal hoof conditioner has no inert ingredients; thus, the afore-described ingredients all have specific purposes in the natural moisturizing, conditioning and healing of the cracks in the hoofs. In addition, the animal hoof conditioner is contained in a lightweight, portable container that includes a brush integrally attached to the container lid or cap so that the conditioner can be easily brushed onto the cracks for penetration therein without causing any inconvenience or discomfort to the horse.

It is an objective of the present invention to provide an animal hoof conditioner that utilizes natural ingredients thereby providing a natural healing process.

It is another objective of the present invention to provide an animal hoof conditioner capable of moisturizing and healing the dry hooves of an animal, with an especial emphasis for use on the hoofs of horses.

It is still yet another objective of the present invention to provide an animal hoof conditioner that heals painful quarter cracks of horses' hoofs and thus prevents further cracking and subsequent damage to the hoofs.

It is yet another objective of the present invention to provide an animal hoof conditioner that can be easily applied to the horse hoof without causing the horse discomfort during the application process.

Still yet another objective of the present invention is to provide an animal hoof conditioner that quickly penetrates the hoof wall for expediting the moisturizing and healing process.

A still yet further objective of the present invention is to provide an animal hoof conditioner that softens and heals the sore and dry hoofs of the animal.

Still yet another objective of the present invention is to provide an animal hoof conditioner whose application gives horses stronger and healthier hoofs.

Still yet a further objective of the present invention is to provide an animal hoof conditioner whose application softens the horse hoofs so that the hoofs are easier to work on.

Yet another objective of the present invention is to provide an animal hoof conditioner that includes ingredients that give a glossy, shiny appearance to the hoofs for enhancing the appearance of show horses.

These and other objects, features and advantages will become apparent to those skilled in the art upon a perusal of

BRIEF DESCRIPTION OF THE DRAWINGS

FIG. 3 is a sectioned elevational view taken along lines 3-3 of FIG. 2 illustrating the permeation of the conditioner within the gaps and fissures of the quarter cracks;

FIG. 4 is a perspective of the applicator brush and container for the animal hoof conditioner; and FIG. 5 is a table listing of the ingredients of the animal hoof conditioner of the present invention.

DETAILED DESCRIPTION OF THE PREFERRED EMBODIMENT

Figure 1:
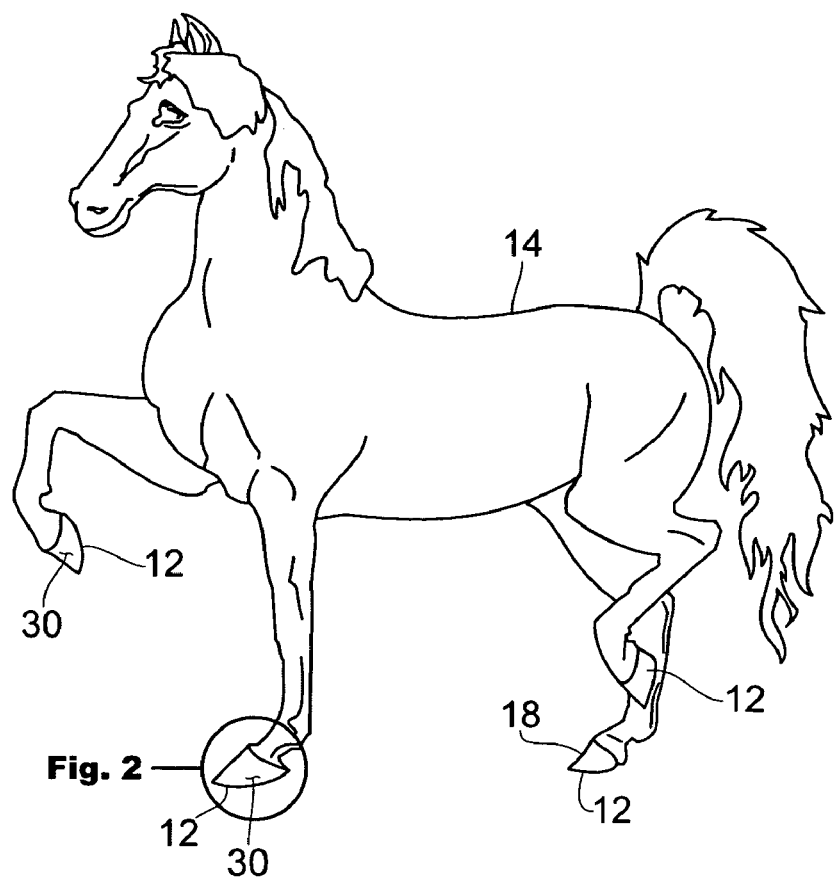
FIG. 1 is a perspective view of an animal, specifically a horse, illustrating a cracked hoof to which the animal hoof conditioner is applied.
Figure 2:
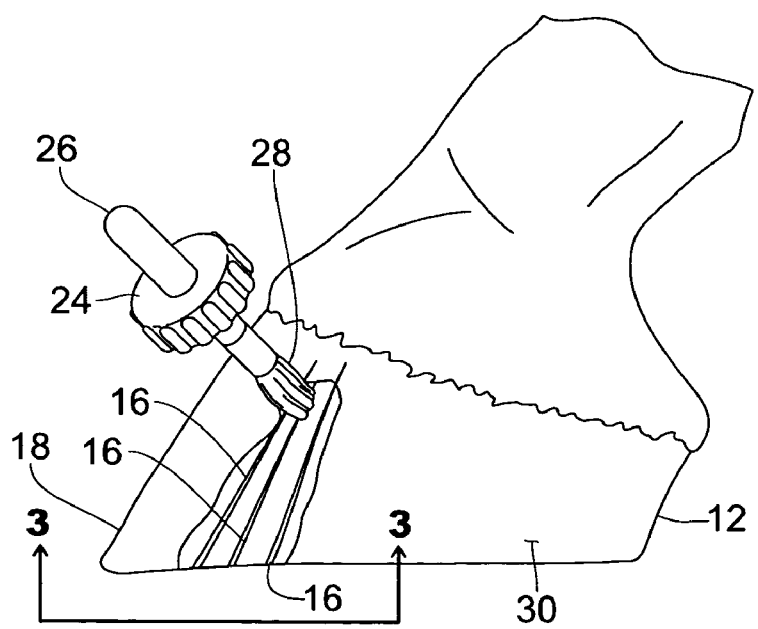
FIG. 2 is an enlarged sectioned view of the horse's hoof first shown in FIG. 1 illustrating the application of the animal hoof conditioner to several quarter cracks extending along the horse's hoof.

Illustrated in FIGS. 1-5 is a composition or treatment for animal hoofs; and, more specifically, a composition or set of ingredients in the form of an animal hoof conditioner 10 for application on the hoofs 12 of horses 14 such as shown in FIGS. 1-3. The animal hoof conditioner 10 is derived from natural ingredients to provide a natural moisturizing and healing for the hoofs 12 of the horse 14 as part of their general care and grooming. In addition, the liquid animal conditioner 10 is also designed to heal cracks 16, such as quarter cracks and sand cracks, that generally extend longitudinally and vertically on the hoof 12, and to prevent further cracking along the hoof 12. The natural ingredients of the animal hoof conditioner 10 facilitate the moisturizing and healing process, and are able to penetrate the wall 18 of the hoof 12 at a more rapid rate for moisturizing and healing the hoofs 12.

As illustrated in FIG. 5, the ingredients for the liquid animal hoof conditioner 10 are listed in the ingredients table or chart 20 and include: aloe vera, specifically whole leaf aloe vera in the percentage of 39.75; linseed oil (flax seed oil) in the percentage of 19.75; turpentine in the percentage of 19.75; pine tar in the percentage of 19.75; and an emulsifier in the percentage of at least 1.0. The whole leaf aloe vera is the ingredient that provides the natural healing agent, the pine tar is the ingredient that adds a shine or gloss to the hoofs 12, which is especially desirable if the horse is a show horse, the linseed oil is the ingredient that provides for the moisturizing effects, and the turpentine is used to thin the pine tar. The emulsifier facilitates the intermixing of the ingredients so that the animal hoof conditioner 10 can be consistently and uniformly applied to the horse's 14 hoof 12.

As shown in FIGS. 2 and 4, the liquid animal hoof conditioner 10 is held within a portable bottle, container or dispenser 22. The container 22 includes a screw on lid or cap 24 having a handle 26 projecting therefrom. In addition, the cap 24 includes an integral brush 28 for applying the animal hoof conditioner 10 to the cracks 16 as shown most distinctly in FIG. 2. Several cracks 16 are shown extending along the hoof 12 in FIG. 2, and are in the process of having the animal hoof conditioner 10 being applied by the brush 28. FIG. 3 shows the penetration of the animal hoof conditioner 10 within and throughout one crack 16 after application by the brush 28.

One representative method of applying the animal conditioner 10 to the horse's 14 hoof 12 is as follows. First, the farrier or horse owner should thoroughly clean the outside or exterior surface 30 of the hoof 12 with a brush or broom. Then the user should vigorously shake the conditioner bottle 22 before opening. The animal conditioner 10 would then be applied to the outside 30 of the hoof 12 with the brush 28 as one would apply paint to a surface. The conditioner 10 should be generously brushed on and the penetrating ability of the conditioner 10 within the cracks 16 will be readily discernible. For cracks 16 such as quarter cracks or sand cracks, a regimen comprising the daily application of the conditioner 10 for two weeks followed by an application every two days for two months should be followed. If the cracks 16 persist the farrier or veterinarian should be contacted; however, as long as the hoofs 12 are kept properly trimmed the cracks 16 will eventually grow out.

In addition, the animal hoof conditioner 10 should be liberally applied for at least six weeks on dry or hard hoofs to prevent further damage thereto, and during summer months the animal hoof conditioner 10 should be used at least once a week for normal health maintenance.

While the present invention has been described with respect to a specific embodiment, it will be understood by those skilled in the art the various changes, modifications and alterations are possible and practicable to one skilled in the art and will still be encompassed by the detailed description set forth herein and fall within the scope of the appended claims.

I claim:

1. A liquid animal hoof conditioner for application to cracks that occur on a hoof of an animal, said conditioner comprising:
    39.75 percent by weight of whole leaf aloe vera;
    19.75 percent by weight of flax seed oil;
    19.75 percent by weight of turpentine; and
    1.0 percent by weight of an emulsifier,
    wherein said weight percents are percent by weight of the conditioner.

2. A kit comprising:
    a portable container holding therein the animal hoof conditioner of claim 1 from which the conditioner can be dispensed; and
    a removable cap secured to the container, the cap having an integral brush for applying the conditioner to cracks on animal's hooves and for moisturizing and protecting the animal's hooves.

* * * * *